US012681000B2

(12) United States Patent
Heidari

(10) Patent No.:    US 12,681,000 B2
(45) Date of Patent:        Jul. 14, 2026

(54) STABILITY CHECK FOR THERMAL COMPOSITIONAL SIMULATION

(71) Applicant: SCHLUMBERGER TECHNOLOGY CORPORATION, Sugar Land, TX (US)

(72) Inventor: Mohammad Reza Heidari, Abingdon (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 553 days.

(21) Appl. No.: 17/998,723

(22) PCT Filed: May 13, 2021

(86) PCT No.: PCT/US2021/032255
§ 371 (c)(1),
(2) Date: Nov. 14, 2022

(87) PCT Pub. No.: WO2021/231731
PCT Pub. Date: Nov. 18, 2021

(65) Prior Publication Data
US 2023/0273179 A1      Aug. 31, 2023

Related U.S. Application Data

(60) Provisional application No. 63/025,259, filed on May 15, 2020.

(51) Int. Cl.
*G01N 33/28*        (2006.01)
*G06F 30/28*        (2020.01)
*G06F 113/08*        (2020.01)

(52) U.S. Cl.
CPC ......... *G01N 33/2823* (2013.01); *G06F 30/28* (2020.01); *G06F 2113/08* (2020.01)

(58) Field of Classification Search
CPC . G01N 33/2823; G06F 30/28; G06F 2113/08; G06F 2113/14; G06F 30/20;
(Continued)

(56) References Cited

U.S. PATENT DOCUMENTS

| | | | |
|---|---|---|---|
| 6,230,101 B1 | 5/2001 | Wallis | |
| 2006/0184329 A1* | 8/2006 | Rowan | ................... G01V 11/00 |
| | | | 702/50 |

(Continued)

OTHER PUBLICATIONS

Ran Gao, "Hybrid Newton-Successive Substitution Method for Multiphase Rachford-Rice Equations", MDPI, Jun. 9, 2018, pmc. ncbi.nlm.nih.gov/articles/PMC7512970/pdf/entropy-20-00452.pdf(Year: 2018).*

(Continued)

*Primary Examiner* — Yossef Korang-Beheshti
(74) *Attorney, Agent, or Firm* — Kyle R. Miiller

(57)        ABSTRACT

Systems and methods are provided for determining a phase state of a thermal compositional fluid sample. An exemplary method includes: providing a first set of parameters from an oilfield operation for a thermal compositional fluid sample; constructing a mass balance function for testing whether a phase of the thermal compositional fluid sample exists; inputting a sequence of time-steps to a numerical iterations technique; solving a system of nonlinear mass and energy conservation equations associated with the thermal compositional fluid sample; determining whether the system of nonlinear mass and energy conservation equations converges to provide a first solution; determining an existing phase state of the thermal compositional fluid sample; performing a stability test on the existing phase of the thermal compositional fluid sample; determining whether the thermal compositional fluid sample includes a new phase state; and updating the first set parameters based on the results from the stability test.

18 Claims, 7 Drawing Sheets

(58) Field of Classification Search
 CPC ...... G06F 30/23; G06F 17/11; G06F 2111/10;
   E21B 2200/20; G01V 99/00; G01V 9/00
 See application file for complete search history.

(56) References Cited

U.S. PATENT DOCUMENTS

| | | | | |
|---|---|---|---|---|
| 2007/0282582 | A1* | 12/2007 | Saaf ........................ | G06F 30/20 |
| | | | | 703/10 |
| 2011/0077922 | A1 | 3/2011 | Moncorge | |
| 2011/0320047 | A1 | 12/2011 | Stone | |
| 2014/0343909 | A1* | 11/2014 | Guerillot ................ | G01V 20/00 |
| | | | | 703/2 |
| 2016/0084080 | A1* | 3/2016 | Lawson ................ | E21B 49/088 |
| | | | | 702/13 |
| 2018/0045046 | A1* | 2/2018 | Stone ...................... | E21B 49/08 |
| 2019/0093469 | A1* | 3/2019 | Williams ................ | E21B 44/00 |
| 2019/0292884 | A1 | 9/2019 | McClure | |

OTHER PUBLICATIONS

International Preliminary Report on Patentability of International
Patent Application No. PCT/US2021/032255 issued on Nov. 24,
2022, 9 pages.
Michelsen, M. L., "Some Aspects of Multiphase Calculations",
Fluid Phase Equilibria, 30 (1986), 15-29.
Brantferger, K.M., Pope, G.A., Sepehrnoori, K., 1991. Development
of a Thermodynamically Consistent, Fully Implicit, Equation-of-
State, Compositional Steamflood Simulator, SPE 21253 presented
at the 11th Symposium on Reservoir Simulation, Anaheim, Cali-
fornia, Feb. 17-20, 1991, pp. 471-480.
Michelsen, M. L., "State Function Based Flash Specifications",
Fluid Phase Equilibria 158-160 (1999), 617-626.
Search Report and Written Opinion of International Patent Appli-
cation No. PCT/US2021/032255 issued on Aug. 10, 2021; 14 pages.
Agarwal R.K., Li Y-K., Nghiem L.X. and Coombe D.A., 1991.
Multiphase Multicomponent Isenthalpic Flash Calculations, Journal
of Canadian Petroleum Technology, vol. 30, No. 3, May-Jun. 1991,
pp. 69-75.
Heidari M., Nghiem L. X., Maini B. B., 2014. Improved Isenthalpic
Multiphase Flash Calculations for Thermal Compositional Simula-
tors. SPE 170029 MS presented at the SPE Heavy Oil Conference
Canada, Alberta, Canada, Jun. 10-12, 2014, 13 pages.
Lapene A., Nichita D. V., Debenest G., Quintard J., 2010. Three-
Phase Free-Water Flash Calculations Using New Modified Rachford-
Rice Equation, Fluid Phase Equilibria 297: 121-128.
Rachford H H Jr., Rice J. D., 1952. Procedure for Use of Electric
Digital Computers in Computers in Calculating Flash Vaporization
Hydrocarbon Equilibrium, JPT 19, also 952327-G SPE Journal
Paper—1952, pp. 327-328.
Stone T. W., Nolen J. S., 2009. Practical and Robust Isenthalpic/
Isothermal Flashes for Thermal Fluids. SPE 118893 presented at the
SPE Reservoir Simulation Symposium, Texas, Feb. 2-4, 2009, 19
pages.
Naccache, P. F., 1997. A Fully-Implicit Thermal Reservoir Simu-
lator, SPE 37985 presented at the 14th SPE Symposium on Reser-
voir Simulation, Dallas, Texas, USA, Jun. 8-11, 1997.
Stone, T. W.; Bennett, J.; Chang, Yih-Bor; 2015. A Comparison of
Thermal Flashes for Systems with Heavy Oil and Component
Solubility in Water. WHOC15—212 presented at the 2015 World
Heavy Oil Congress, Edmonton, Alberta, Canada., 12 pages.
Extended Search Report issued in European Patent Application No.
21803128.4 dated May 29, 2024, 9 pages.

* cited by examiner

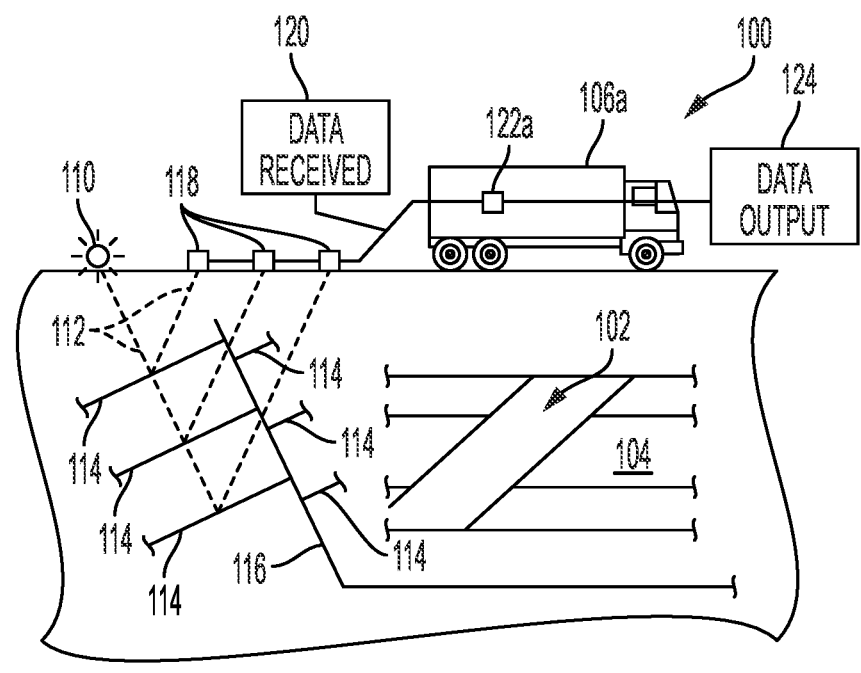
FIG. 1A
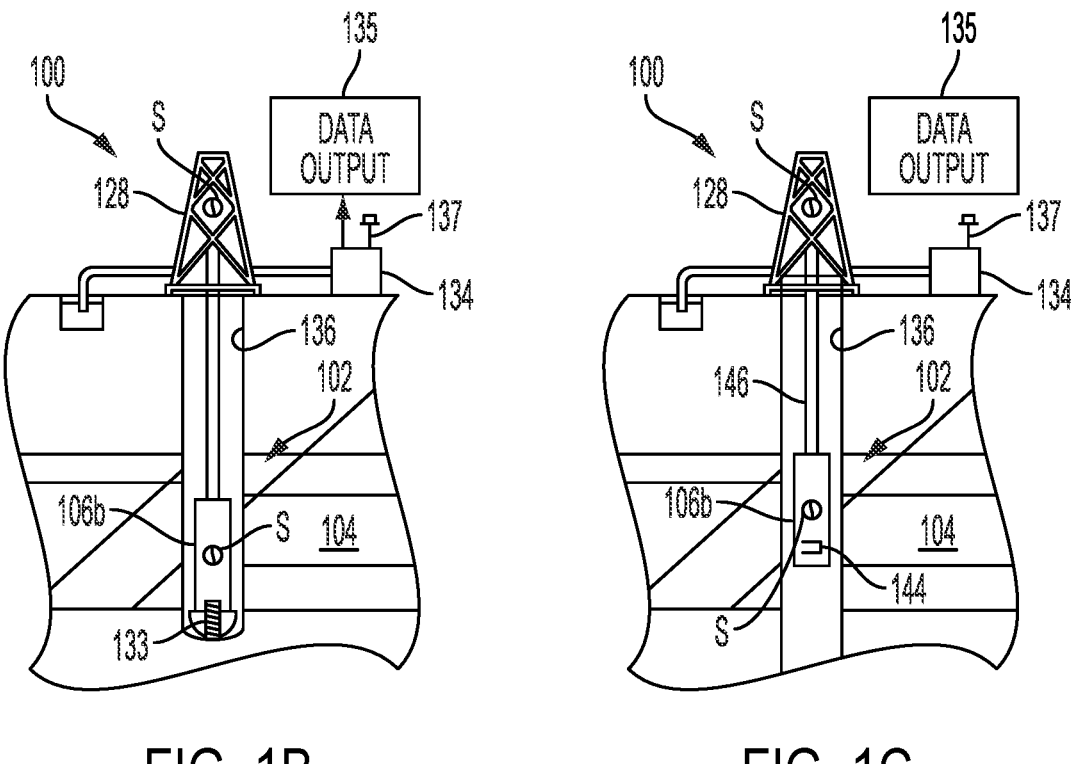
FIG. 1B          FIG. 1C

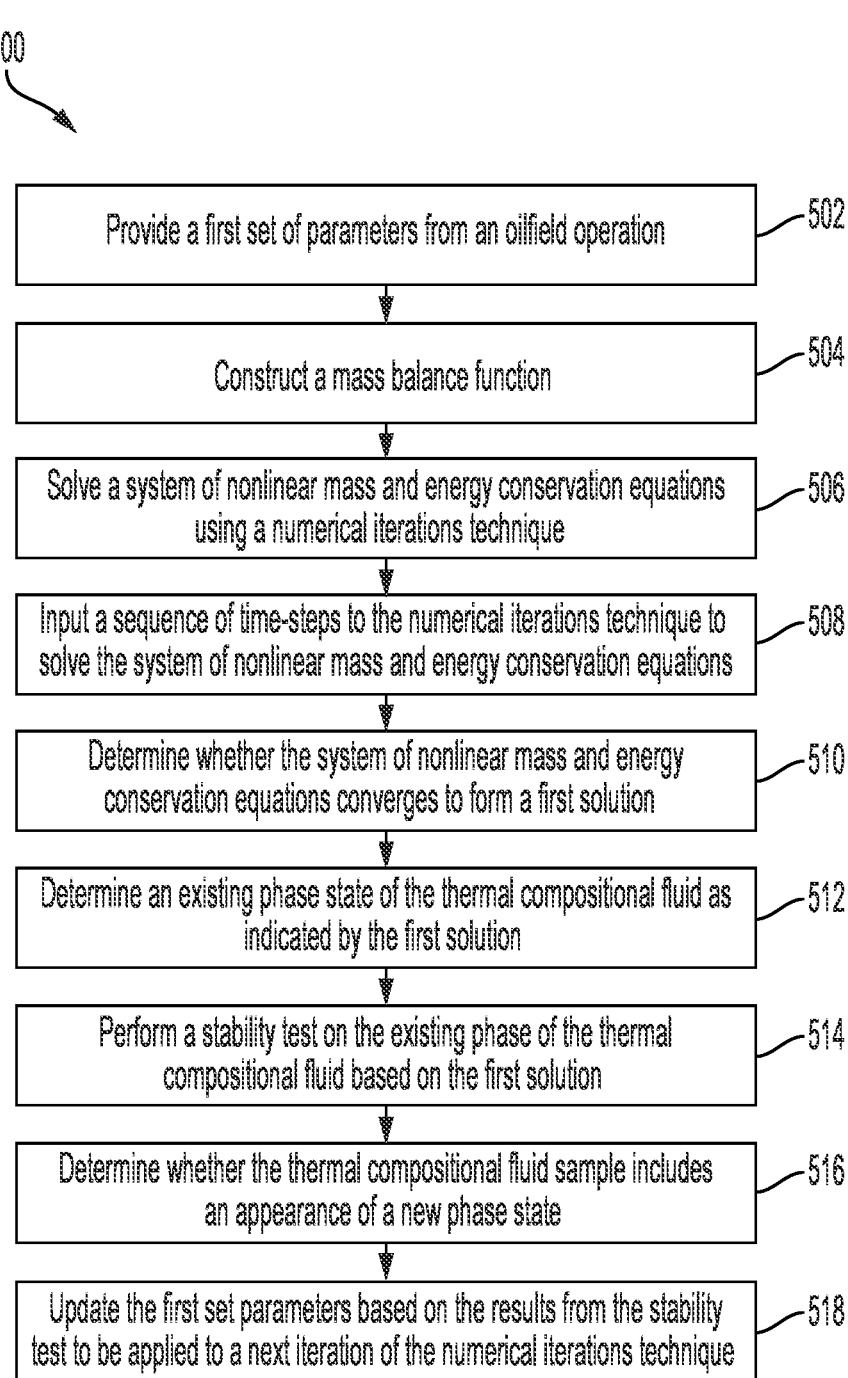

500

Provide a first set of parameters from an oilfield operation — 502

Construct a mass balance function — 504

Solve a system of nonlinear mass and energy conservation equations using a numerical iterations technique — 506

Input a sequence of time-steps to the numerical iterations technique to solve the system of nonlinear mass and energy conservation equations — 508

Determine whether the system of nonlinear mass and energy conservation equations converges to form a first solution — 510

Determine an existing phase state of the thermal compositional fluid as indicated by the first solution — 512

Perform a stability test on the existing phase of the thermal compositional fluid based on the first solution — 514

Determine whether the thermal compositional fluid sample includes an appearance of a new phase state — 516

Update the first set parameters based on the results from the stability test to be applied to a next iteration of the numerical iterations technique — 518

FIG. 5

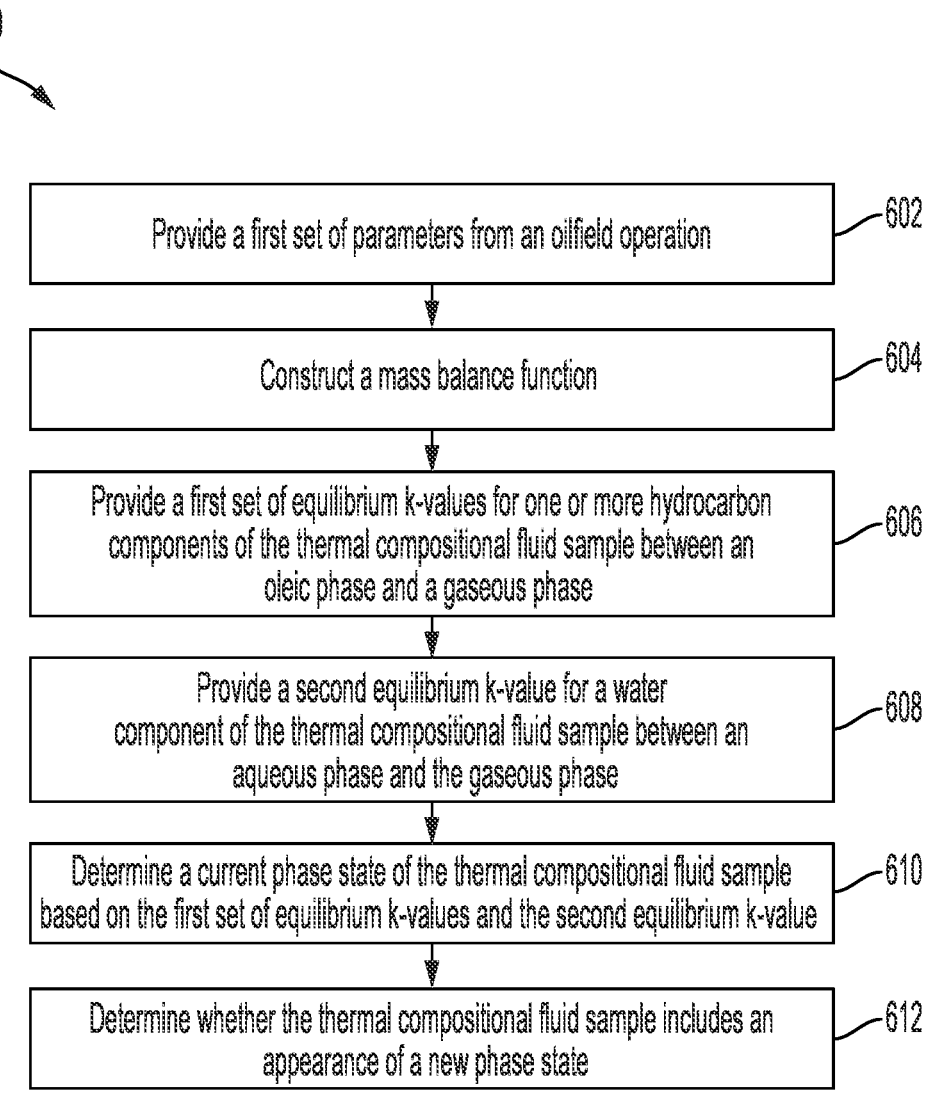

600

Provide a first set of parameters from an oilfield operation ——602

Construct a mass balance function ——604

Provide a first set of equilibrium k-values for one or more hydrocarbon components of the thermal compositional fluid sample between an oleic phase and a gaseous phase ——606

Provide a second equilibrium k-value for a water component of the thermal compositional fluid sample between an aqueous phase and the gaseous phase ——608

Determine a current phase state of the thermal compositional fluid sample based on the first set of equilibrium k-values and the second equilibrium k-value ——610

Determine whether the thermal compositional fluid sample includes an appearance of a new phase state ——612

FIG. 6

STABILITY CHECK FOR THERMAL COMPOSITIONAL SIMULATION

CROSS REFERENCE TO RELATED APPLICATIONS

This application is a National Stage Entry of International Application No. PCT/US2021/032255, filed on May 13, 2021, which claims priority to U.S. provisional application No. 63/025,259 filed on May 15, 2020, the contents of which is included herein in its entirety.

BACKGROUND

Natural gas and crude oil are naturally occurring hydrocarbon mixtures that are found underground and at elevated conditions of pressure and temperature. They are generally referred to as petroleum fluids. Petroleum fluids are principally made up of hydrocarbons, but a few non-hydrocarbon components may be present such as nitrogen, carbon dioxide and hydrogen sulfide.

As the conditions of pressure and temperature vary, the phases in which hydrocarbons exist, and the composition of the phases may change. It is important to understand the initial condition of fluids to be able to calculate surface volumes represented by subsurface hydrocarbons. It is also helpful to be able to predict phase changes as the temperature and pressure vary both in the reservoir and as the fluids pass through the surface facilities, so that the appropriate subsurface and surface developments plans can be made. Phase behavior describes the phase or phases in which a mass of fluid exists at given conditions of pressure, volume and temperature (PVT).

When fluids are produced from a subsurface reservoir to the surface both temperature and pressure are reduced. The pressure and temperature (P-T) changes result in two kinds of phase change in the produced fluids: 1.) Liquid may condense from the produced gas; and 2.) Gas may evolve from the produced liquid. Similar changes take place in the subsurface reservoir as a result of the isothermal (constant temperature) pressure change generated by fluid production: 1.) Condensate (liquid) may be produced in the reservoir from the gas phase. 2. Solution gas may be evolved in the reservoir from the liquid phase.

Regardless of the aspect of petroleum extraction process—be it drilling, reservoir estimation, reservoir performance analysis, reservoir simulation, tubing flow hydraulics, gathering design, gas-liquid separation, oil and gas transmission, oil and gas metering or quality control—a good predictive knowledge of phase behavior is needed.

BRIEF DESCRIPTION OF THE DRAWINGS

For a better understanding of the aforementioned embodiments as well as additional embodiments thereof, reference should be made to the Detailed Description below, in conjunction with the following drawings in which like reference numerals refer to corresponding parts throughout the figures.

FIG. 1A illustrates a simplified schematic view of a survey operation performed by a survey tool at an oil field, in accordance with some embodiments.

FIG. 1B illustrates a simplified schematic view of a drilling operation performed by drilling tools, in accordance with some embodiments.

FIG. 1C illustrates a simplified schematic view of a production operation performed by a production tool, in accordance with some embodiments.

FIG. 5 illustrates a workflow of a method for determining a phase state of a thermal compositional fluid sample, in accordance with some embodiments.

FIG. 6 illustrates a workflow of another method for determining a phase state of a thermal compositional fluid sample, in accordance with some embodiments.

BRIEF SUMMARY

Figure 2:
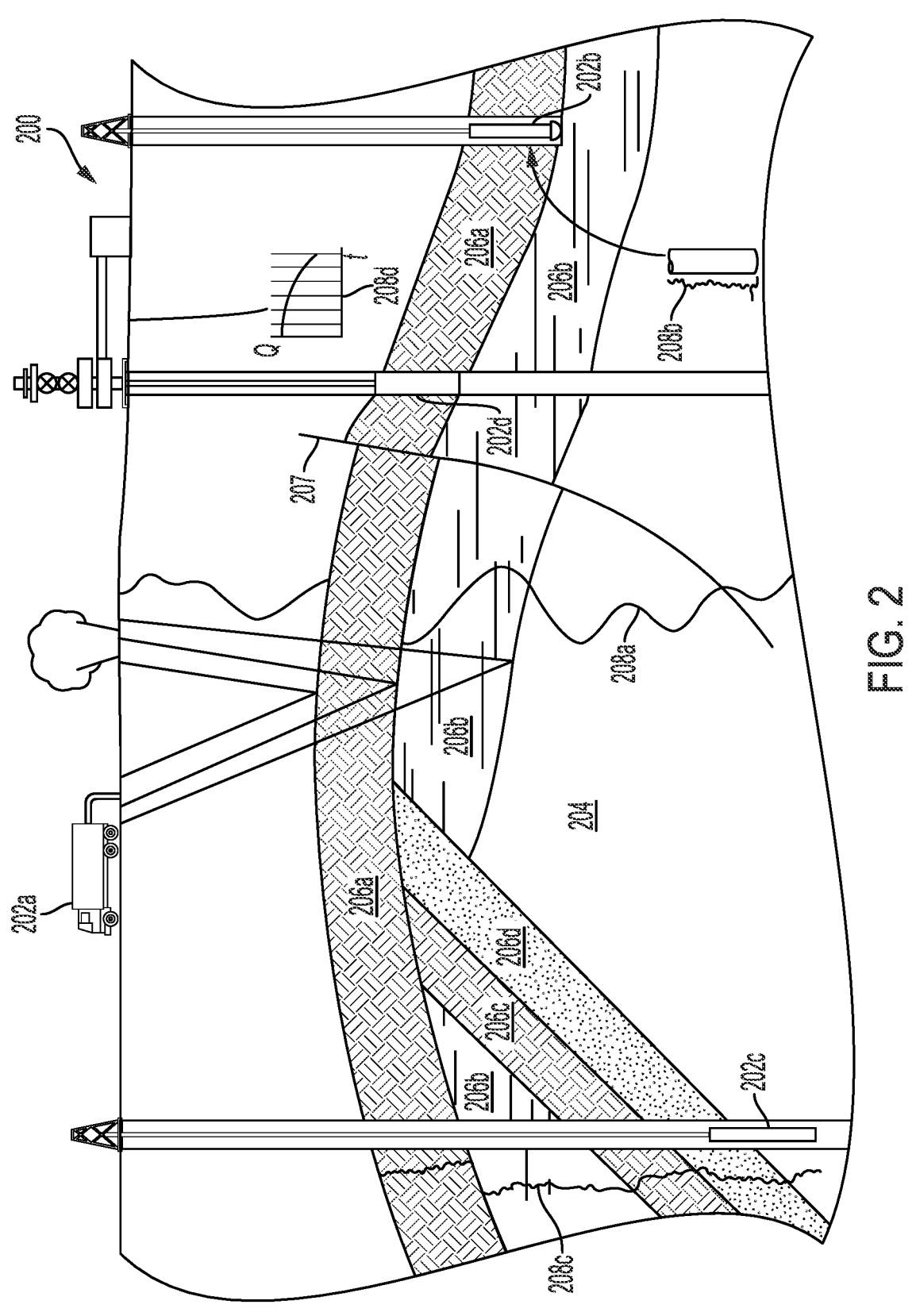
FIG. 2 illustrates a schematic view, partially in cross section, of an oilfield, in accordance with some embodiments.

According to one aspect of the subject matter described in this disclosure, a method for determining a phase state of a thermal compositional fluid sample is provided. The method includes the following: providing, using one or more computing device processors, a first set of parameters from an oilfield operation for a thermal compositional fluid sample; constructing, using the one or more computing device processors, a mass balance function for testing whether a phase of the thermal compositional fluid sample exists based on the first of parameters; inputting, using the one or more computing device processors, a sequence of time-steps to a numerical iterations technique based on the mass balance function; solving, using the one or more computing device processors, a system of nonlinear mass and energy conservation equations associated with the thermal compositional fluid sample using the numerical iterations technique; determining, using the one or more computing device processors, whether the system of nonlinear mass and energy conservation equations converges over a single step to provide a first solution to the system of nonlinear mass and energy conservation equations; in response to the system of nonlinear mass and energy conservation equations converging, determining, using the one or more computing device processors, an existing phase state of the thermal compositional fluid sample as indicated by the first solution; in response to determining the existing phase state, performing, using the one or more computing device processors, a stability test on the existing phase of the thermal compositional fluid sample based on the first solution; determining, using the one or more computing device processors, whether the thermal compositional fluid sample includes an appearance of a new phase state based on results from the stability test; and updating, using the one or more computing device processors, the first set parameters based on the results from the stability test to be applied to a next iteration of the numerical iterations technique.

According to another aspect of the subject matter described in this disclosure, a method for determining a phase state of a thermal compositional fluid sample is provided. The method includes the following: providing, using one or more computing device processors, a first set of parameters from an oilfield operation for a thermal compositional fluid sample; constructing, using the one or more computing device processors, a mass balance function for testing whether a phase of the thermal compositional fluid sample exists based on the first of parameters; providing, using the one or more computing device processors, a first set of equilibrium k-values for one or more hydrocarbon components of the thermal compositional fluid sample between an oleic phase and a gaseous phase based on the mass balance function; providing, using the one or more computing device processors, a second equilibrium k-value for a water component of the thermal compositional fluid sample between an aqueous phase and the gaseous phase; determining, using the one or more computing device processors, a current phase state of the thermal compositional fluid sample based on the first set of equilibrium k-values and the second equilibrium k-value; and in response to determining the current phase state of the thermal compositional fluid sample, determining, using the one or more computing device processors, whether the thermal compositional fluid sample includes an appearance of a new phase state based on the current phase state of the thermal compositional fluid sample.

According to another aspect of the subject matter described in this disclosure, a system for determining a phase state of a thermal compositional fluid sample, is provided. The system includes one or more computing device processors. Also, the system includes one or more computing device memories, coupled to the one or more computing device processors. The one or more computing device memories stores instructions executed by the one or more computing device processors. The instructions are configured to: provide a first set of parameters from an oilfield operation for a thermal compositional fluid sample; construct a mass balance function for testing whether a phase of the thermal compositional fluid sample exists based on the first of parameters; input a sequence of time-steps to a numerical iterations technique based on the mass balance function; solve a system of nonlinear mass and energy conservation equations associated with the thermal compositional fluid sample using the numerical iterations technique; determine whether the system of nonlinear mass and energy conservation equations converges over a single step to provide a first solution to the system of nonlinear mass and energy conservation equations; in response to the system of nonlinear mass and energy conservation equations converging, determine an existing phase state of the thermal compositional fluid sample as indicated by the first solution; in response to determining the existing phase state, perform a stability test on the existing phase of the thermal compositional fluid sample based on the first solution; determine whether the thermal compositional fluid sample includes an appearance of a new phase state based on results from the stability test; and update the first set of parameters based on the results from the stability test to be applied to a next iteration of the numerical iterations technique.

Additional features and advantages of the present disclosure are described in, and will be apparent from, the detailed description of this disclosure.

DETAILED DESCRIPTION

Reference will now be made in detail to embodiments, examples of which are illustrated in the accompanying drawings and figures. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits and networks have not been described in detail so as not to unnecessarily obscure aspects of the embodiments.

It will also be understood that, although the terms first, second, etc., may be used herein to describe various elements, these elements should not be limited by these terms. These terms are used to distinguish one element from another. For example, a first object or step could be termed a second object or step, and, similarly, a second object or step could be termed a first object or step, without departing from the scope of the present disclosure. The first object or step, and the second object or step, are both objects or steps, respectively, but they are not to be considered the same object or step.

The terminology used in the detailed description herein is for the purpose of describing particular embodiments and is not intended to be limiting of the present disclosure. As used in the detailed description and the appended claims, the singular forms "a," "an" and "the" are intended to include the plural forms as well, unless the context clearly indicates otherwise. It will also be understood that the term "and/or" as used herein refers to and encompasses any possible combination of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context.

Those with skill in the art will appreciate that while some terms in this disclosure may refer to absolutes, e.g., each of a plurality of objects, etc., the methods and techniques disclosed herein may also be performed on fewer than all of a given thing, e.g., performed on one or more components and/or performed on one or more objects. Accordingly, in instances in the disclosure where an absolute is used, the disclosure may also be interpreted to be referring to a subset.

The disclosure describes a system and a method for calculating a phase state of a fluid sample in a thermal compositional process that may include field operations or software such as a reservoir simulator. The method allows business planning for oil and gas companies through simulation and prediction of oilfields with reservoir and surface network simulation, stand-alone PVT analysis for reserves estimation and production monitoring, well analysis and fluid sample analysis for characterization of fluids. The disclosure describes a robust means to evaluate both the state of a multi-component, multi-phase fluid and the vapor-liquid equilibrium (VLE).

The methods described herein improve previous techniques by providing a fast and reliable way of determining oil, water, and gas phase boundaries. Moreover, the methods described herein are simpler and quicker to calculate oil, water, and gas phase boundaries and may not need heuristics used in other commonly known approaches. Also, the methods described herein may be implemented to work closely with nonlinear solvers having nonlinear update cycles within a simulator to improve stability and provide for faster run times with improved accuracy.

In addition, the system and methods described herein may be applicable to or work in conjunction with various flow meters, such as a Schlumberger Vx flow meter. In some embodiments, the flow meters measure the flow of fluids across a venturi using gamma ray spectroscopy, which is a measure of the molar rate of various components including hydrocarbon and water. If the reservoir fluids are sufficiently characterized such that their equilibrium k-values are known as a function of temperature, then the molar flow information from the flow meter together with a pressure and temperature measurement may be used to determine which phases are present in the fluid system. Flow meters are used throughout a recovery pipeline such as in surface facilities and downhole.

The disclosure describes using basic constitutive equations to test for the existence of oleic, gaseous and aqueous phases in a thermal compositional fluid sample. In one embodiment, a mass balance function is constructed that is monotone in the gas phase split. Input data to the mass balance function may be measured and acquired in surface or downhole pipelines and wells, such as pressure, temperature and component molar rates. In addition, the characterization of hydrocarbon components of the thermal compositional fluid sample may be required to provide equilibrium k-values between the oleic and gaseous phases. In addition, the characterization of the water component of the thermal compositional fluid sample may be used to provide an equilibrium k-value between the aqueous and gaseous phases.

In some embodiments, the mass balance function may be monotonic for testing the phase of a thermal compositional fluid sample as described herein. In some embodiments, the mass balance function may be a Rachford-Rice function. It is to be appreciated that the mass balance function described herein may also be referred to as a material balance function.

These k-values are measured over a range of temperatures and pressures applicable to the recovery operation and are monotone in temperature. There are additional assumptions regarding solubility of the hydrocarbon and water components such that hydrocarbon components are not soluble in the aqueous phase and the water component is not soluble in the oleic phase. Although restrictive, the above assumptions nonetheless cover a wide range of typical thermal oilfield recovery processes. Given the simplicity and calculation efficiency of these methods, the present disclosure has a wide variety of applications, such as both in pipeline and reservoir simulation software, surface and downhole flow metering as well as sample characterization of equilibrium states.

The particulars shown herein are by way of example and for purposes of illustrative discussion of the embodiments of the present disclosure only and are presented in the cause of providing what is believed to be the most useful and readily understood description of the principles and conceptual aspects of the present disclosure. In this regard, no attempt is made to show structural details in more detail than is necessary for the fundamental understanding of the present disclosure, the description taken with the drawings making apparent to those skilled in the art how the several forms of the subject disclosure may be embodied in practice. Furthermore, like reference numbers and designations in the various drawings indicate like elements.

FIGS. 1A-1C illustrate simplified, schematic views of oilfield 100 having subterranean formation 102 containing reservoir 104 therein in accordance with implementations of various technologies and techniques described herein. FIG. 1A illustrates a survey operation being performed by a survey tool, such as seismic truck 106a, to measure properties of the subterranean formation. The survey operation is a seismic survey operation for producing sound vibrations. In FIG. 1A, one such sound vibration, e.g., sound vibration 112 generated by source 110, reflects off horizons 114 in earth formation 116. A set of sound vibrations is received by sensors, such as geophone-receivers 118, situated on the earth's surface. The data received 120 is provided as input data to a computer 122a of the seismic truck 106a, and responsive to the input data, computer 122a generates seismic data output 124. This seismic data output may be stored, transmitted or further processed as desired, for example, by data reduction.

FIG. 1B illustrates a drilling operation being performed by drilling tools 106b suspended by rig 128 and advanced into subterranean formations 102 to form wellbore 136. The drilling tools are advanced into subterranean formations 102 to reach reservoir 104. Each well may target one or more reservoirs. The drilling tools may be adapted for measuring downhole properties using logging while drilling tools. The logging while drilling tools may also be adapted for taking core sample 133 as shown.

The drilling tool 106b may include downhole sensor S adapted to perform well testing and well logging while drilling (LWD) data collection. The sensor S may be any type of sensor. The data collected may be pressure, temperature, or the like.

Computer facilities may be positioned at various locations about the oilfield 100 (e.g., the surface unit 134) and/or at remote locations. Surface unit 134 may be used to communicate with the drilling tools and/or offsite operations, as well as with other surface or downhole sensors. Surface unit 134 is capable of communicating with the drilling tools to send commands to the drilling tools, and to receive data therefrom. Surface unit 134 may also collect data generated during the drilling operation and produce data output 135, which may then be stored or transmitted.

In some embodiments, sensors (S), such as gauges, may be positioned about oilfield 100 to collect data relating to various oilfield operations as described previously. As shown, sensor (S) is positioned in one or more locations in the drilling tools and/or at rig 128 to measure drilling parameters, such as weight on bit, torque on bit, pressures, temperatures, flow rates, compositions, rotary speed, and/or other parameters of the field operation. In some embodiments, sensors (S) may also be positioned in one or more locations in the wellbore 136.

Drilling tools 106b may include a bottom hole assembly (BHA) (not shown), generally referenced, near the drill bit (e.g., within several drill collar lengths from the drill bit). The bottom hole assembly includes capabilities for measuring, processing, and storing information, as well as communicating with surface unit 134. The bottom hole assembly further includes drill collars for performing various other measurement functions.

The bottom hole assembly may include a communication subassembly that communicates with surface unit 134. The communication subassembly is configured to send signals to and receive signals from the surface using a communications channel such as mud pulse telemetry, electro-magnetic telemetry, or wired drill pipe communications. The communication subassembly may include, for example, a transmitter that generates a signal, such as an acoustic or electromagnetic signal, which is representative of the measured drilling parameters. It will be appreciated by one of skill in the art that a variety of telemetry systems may be employed, such as wired drill pipe, electromagnetic or other known telemetry systems.

The data gathered by sensors (S) may be collected by surface unit 134 and/or other data collection sources for analysis or other processing. An example of the further processing is the generation of a grid for use in the computation of a juxtaposition diagram as discussed below. The data collected by sensors (S) may be used alone or in combination with other data. The data may be collected in one or more databases and/or transmitted on or offsite. The data may be historical data, real time data, or combinations thereof. The real time data may be used in real time (considered as substantially instantaneous), or stored for later use. The data may also be combined with historical data or other inputs for further analysis. The data may be stored in separate databases, or combined into a single database.

Surface unit 134 may include transceiver 137 to allow communications between surface unit 134 and various portions of the oilfield 100 or other locations. Surface unit 134 may also be provided with or functionally connected to one or more controllers (not shown) for actuating mechanisms at oilfield 100. Surface unit 134 may then send command signals to oilfield 100 in response to data received. Surface unit 134 may receive commands via transceiver 137 or may itself execute commands to the controller. A processor may be provided to analyze the data (locally or remotely), make the decisions and/or actuate the controller.

FIG. 1C illustrates a production operation being performed by production tool 106c deployed by rig 128 having a Christmas tree valve arrangement into completed wellbore 136 for drawing fluid from the downhole reservoirs into rig 128. The fluid flows from reservoir 104 through perforations in the casing (not shown) and into production tool 106c in wellbore 136 and to rig 128 via gathering network 146.

In some embodiments, sensors (S), such as gauges, may be positioned about oilfield 100 to collect data relating to various field operations as described previously. As shown, the sensors (S) may be positioned in production tool 106c or rig 128.

While FIGS. 1A-1C illustrate tools used to measure properties of an oilfield, it will be appreciated that various measurement tools capable of sensing parameters, such as seismic two-way travel time, density, resistivity, production rate, etc., of the subterranean formation and/or its geological formations may be used. As an example, wireline tools may be used to obtain measurement information related to casing attributes. The wireline tool may include a sonic or ultrasonic transducer to provide measurements on casing geometry. The casing geometry information may also be provided by finger caliper sensors that may be included on the wireline tool. Various sensors may be located at various positions along the wellbore and/or the monitoring tools to collect and/or monitor the desired data. Other sources of data may also be provided from offsite locations.

The field configurations of FIGS. 1A-1C are intended to provide a brief description of an example of a field usable with oilfield application frameworks. Part, or all, of oilfield 100 may be on land, water, and/or sea. Also, while a single field measured at a single location is depicted, oilfield applications may be utilized with any combination of one or more oilfields, one or more processing facilities and one or more wellsites. An example of processing of data collected by the sensors is the generation of a grid for use in the computation of a juxtaposition diagram as discussed below.

FIG. 2 illustrates a schematic view, partially in cross section of oilfield 200 having data acquisition tools 202a,

202b, 202c and 202d positioned at various locations along oilfield 200 for collecting data of subterranean formation 204 in accordance with implementations of various technologies and techniques described herein. Data acquisition tools 202a-202d may be the same as data acquisition tools 106a-106d of FIGS. 1A-1C, respectively, or others not depicted. As shown, data acquisition tools 202a-202d generate data plots or measurements 208a-208d, respectively. These data plots are depicted along oilfield 200 to demonstrate the data generated by the various operations.

Data plots 208a-208c are examples of static data plots that may be generated by data acquisition tools 202a-202c, respectively; however, it should be understood that data plots 208a-208c may also be data plots that are updated in real time (considered as substantially instantaneous). These measurements may be analyzed to better define the properties of the formation(s) and/or determine the accuracy of the measurements and/or for checking for errors. The plots of each of the respective measurements may be aligned and scaled for comparison and verification of the properties.

Static data plot 208a is a seismic two-way response over a period of time. Static plot 208b is core sample data measured from a core sample of the formation 204. The core sample may be used to provide data, such as a graph of the density, porosity, permeability, or some other physical property of the core sample over the length of the core. Tests for density and viscosity may be performed on the fluids in the core at varying pressures and temperatures. Static data plot 208c is a logging trace that provides a resistivity or other measurement of the formation at various depths.

A production decline curve or graph 208d is a dynamic data plot of the fluid flow rate over time. The production decline curve provides the production rate as a function of time. As the fluid flows through the wellbore, measurements are taken of fluid properties, such as flow rates, pressures, composition, etc.

Other data may also be collected, such as historical data, user inputs, economic information, and/or other measurement data and other parameters of interest. As described below, the static and dynamic measurements may be analyzed and used to generate models of the subterranean formation to determine characteristics thereof. Similar measurements may also be used to measure changes in formation aspects over time.

The subterranean structure 204 has a plurality of geological formations 206a-206d. As shown, this structure has several formations or layers, including a shale layer 206a, a carbonate layer 206b, a shale layer 206c and a sand layer 206d. A fault 207 extends through the shale layer 206a and the carbonate layer 206b. The static data acquisition tools are adapted to take measurements and detect characteristics of the formations.

While a specific subterranean formation with specific geological structures is depicted, it will be appreciated that oilfield 200 may contain a variety of geological structures and/or formations, sometimes having extreme complexity. In some locations, for example below the water line, fluid may occupy pore spaces of the formations. Each of the measurement devices may be used to measure properties of the formations and/or its geological features. While each acquisition tool is shown as being in specific locations in oilfield 200, it will be appreciated that one or more types of measurements may be taken at one or more locations across one or more fields or other locations for comparison and/or analysis.

The data collected from various sources, such as the data acquisition tools of FIG. 2, may then be processed and/or evaluated to form reservoir models for assessing a drill site. Moreover, the flow meters described herein may work in conjunction with structures described in FIGS. 1A-1B and FIG. 2 to measure the molar rate of various components including hydrocarbon and water. The exemplary collected data described herein may be use as inputs for the methods described hereafter.

In some embodiments, the model may include the a well's name, area and location (by latitude and longitude) (county and state) of the well, the well control number, rig contractor name and rig number, spud and rig release dates, weather and temperature, road condition and hole condition, and name of the person submitting the report.

In some embodiments, the model may include bits used (with size and serial numbers), depths (kelly bushing depth, ground elevation, drilling depth, drilling depth progress, water depth), drilling fluid losses and lost circulation, estimated costs (usually a separate document), fishing and side tracking, mud engineer's lithology of formations drilled and hydrocarbons observed, daily drilling issues, tubulars (casing and tubing joints and footages) run and cement used, vendors and their services, well bore survey results, work summary, work performed and planned.

In some embodiments, the model may include the hourly breakdown duration of single operations with codes that allow an instant view, understanding and summary of each phase, for example, rig up and rig down hours, drilling tangent (vertical), curve drilling (to change the direction of the drilling from vertical to horizontal) and lateral drilling (for horizontal wells), circulating the well, conditioning the mud, reaming the hole for safety to prevent stuck pipe, running casing, waiting on cement, nipple up and testing BOP's, trips in and out of the hole and surveys.

The fluid systems described herein may include three phases: aqueous, oleic, and gaseous, as shown in Table 1. Any number of hydrocarbon components (C1, C2, Cx) may be present, also a water component (H2O) may be present. Three assumptions that may be considered are that the hydrocarbon components are not soluble in the aqueous phase, the water component is not soluble in the oleic phase, and that the equilibrium k-values for all components are monotone functions of temperature.

TABLE 1

| Three phases of the fluid systems described herein | | | |
|---|---|---|---|
| | C1 | C2 | Cx | H2O |
| Aqueous | | | | x |
| Oleic | x | x | x | |
| Gaseous | x | x | x | x |

The following definitions are relevant to the present disclosure:

$N_c$, total number of components $x_i$, i'th hydrocarbon component mole fraction in Oleic phase, $i \neq w$ $y_i$, i'th hydrocarbon component mole fraction in Gaseous phase $y_w$, water component in the Gaseous phase $w_i$, i'th component mole fraction in aqueous phase, $i=w$ only L, V, W, oleic, gaseous and aqueous phase mole fractions, moles phase/total moles p, q, intermediate variables defined below with values depending on whether a water phase is present or not G(V), the mass balance function for a given fluid configuration. To solve for equilibrium between phases, set G(V)=0.

$k_i$, the oleic phase to gaseous phase equilibrium k-value, $y_i = k_i(P,T)x_i$, $i \in$ hydrocarbon components.

Constitutive equations relevant to the present disclosure include the following:

$$z_w = y_w V + W \qquad \text{Eq. (1A)}$$

$$z_i = x_i L + y_i V \qquad \text{Eq. (1B)}$$

$$L + V + W = 1 \qquad \text{Eq. (1C)}$$

$$\Sigma_{i=1}^{Nc} y_i = 1 \text{ if } V > 0 \qquad \text{Eq. (1D)}$$

$$\Sigma_{i \neq w} x_i = 1 \text{ if } L > 0 \qquad \text{Eq. (1E)}$$

A Monotonic G(V) when a Water Phase Exists or not

A mass balance function G(V) may form the basis for testing whether a particular phase exists. This section describes how to set up such a function when a water phase exists or not.

Existence of Water Phase

When a water phase exists, then the water phase split is W>0. Given the assumption that only a water component exists in the water phase, then $w_w = 1$ and the water component fraction in the gas phase is $y_w = k_w$. Then $z_w = y_w V + W$ and $L = 1 - V - W = 1 - z_w - V(1 - k_w)$. It is convenient to define two variables p, q such that if W>0, $p = 1 - z_w$ and $q = 1 - k_w$. Using these convenient variables, the expression for L can be written as $L = p - Vq$.

For the i'th hydrocarbon component, using the constitutive equations above and basic assumption of hydrocarbon insolubility in the water phase, the global mole fraction of this component can be expressed as $z_i = x_i(p - Vq) + x_i k_i V$ so that $$x_i = \frac{z_i}{p + V(k_i - q)}.$$

Then a monotonic mass balance function may be $G(V) = \Sigma_{i \neq w} x_i k_i - q \, \Sigma_{i \neq w} x_i$, or $$G(V) = \sum_{i \neq w} \frac{z_i(k_i - q)}{p + V(k_i - q)} \qquad \text{Eq. (2)}$$

Note that all k-values, which are functions of temperature and pressure, and all z are input variables to G(V) so the only independent variable in this function is the gaseous phase split V. Also note that the derivative G'(V)<0, $\forall V$.

When Water Phase does not Exist

For the case where W=0, L=1−V and $z_w = y_w V$, a monotonic G(V) can be shown to be $$G(V) = \left( \sum_{i=1}^{Nc} y_i - 1 \right) - \left( \sum_{i \neq w} x_i - 1 \right) = \sum_{i \neq w} y_i + \frac{z_w}{V} - \sum_{i \neq w} x_i, \qquad \text{Eq. (3)}$$

or $$G(V) = \sum_{i \neq w} \frac{z_i(k_i - 1)}{1 + V(k_i - 1)} + \frac{z_w}{V}$$

Again, note the sign of the derivative is negative, hence this function is monotonic in the independent variable V.

Testing for Phase Existence

Water Phase Existence

Given that $W=z_w-y_w V$, $y_w=k_w$ then if $W>0$, $$\frac{z_w}{k_w} > V \qquad \text{Eq. (4)}$$

If $$\frac{z_w}{k_w} > 1 > V$$

then the water phase exists. If $$\frac{z_w}{k_w} \le 1$$

then $$G\left(V = \frac{z_w}{k_w}\right) \le 0$$

should be evaluated. In order to evaluate this, a property of monotonic functions should be used such that if G is a monotonic function and $G(a)<G(b)$, then $a>b$ provided $G'(V)<0$ for all V. The expressions for $G(V)$ derived in the preceding section satisfy both of these conditions. Therefore to test whether Eq. (4) is true, one can test whether $$G\left(\frac{z_w}{k_w}\right) \le 0 \qquad \text{Eq. (5)}$$

Therefore, the following conditions satisfy the existence of water phase:

$$G\left(\frac{z_w}{k_w}\right) \le 0 \text{ or } \frac{z_w}{k_w} > 1 \qquad \text{Eq. (6)}$$

Gas Phase Existence

Once it is determined whether a water phase exists following the calculations in the preceding section, then existence of a gas phase may be determined as follows.

If a water phase exists, $W>0$. Since the root of the expression $G(V)=0$ finds a gaseous phase split V that determines phase equilibrium between the oleic and gaseous phases, if the monotone function $G(V_{min}=0)<0$, then $V=0$. Using the $G(V)$ in Eq (2) and the expressions for p, q when $W>0$, $$G(V_{min} = 0) = \sum\nolimits_{i \ne w} \frac{z_i(k_i - q)}{p} \le 0,$$

and using the relation $\Sigma_{i \ne w} z_i = p$, then a gas phase exists when $$\Sigma_{i \ne w} z_i k_i > pq \qquad \text{Eq. (7)}$$

If a water phase does not exist but a water component exists, i.e. $z_w>0$, then automatically $V>0$ because the only other place that the water component can exist is in the gas phase. If a water phase does not exist and there is no water in the system, i.e. $z_w=0$, then the mole fractions of oil components in the oleic phase are exactly the feed components of those components, so using the fact that equilibrium k-values $k_i(P,T)$ for both hydrocarbon and water components are monotone functions in temperature T, a gas phase exists if the sum of the gaseous phase component mole fractions exceeds 1, or $$\Sigma_{i \ne w} z_i k_i > 1 \qquad \text{Eq. (8)}$$

Oil Phase Existence

If a water phase exists but an oleic phase does not, then from the constitutive equations the gaseous split is $$V = \frac{p}{q}$$

including its maximum value, so that the function $G(V)$ which is monotone in V must be +ve when an oleic phase is not present, i.e.

$$G(V_{max}) = \sum\nolimits_{i \ne w} \frac{z_i(k_i - q)}{p + \frac{p}{q}(k_i - q)} \ge 0$$

when $L=0$. This can be reduced to $$G(V_{max}) = \sum\nolimits_{i \ne w} \frac{z_i}{k_i} \le \frac{p}{q}$$

when $W>0$, $L=0$. So, in presence of a water phase, an oil phase exists when $$\sum\nolimits_{i \ne w} \frac{z_i}{k_i} > \frac{p}{q} \qquad \text{Eq. (9)}$$

If both aqueous and oleic phases do not exist, $W=0$ and $L=0$, so that $V_{max}=1$. Then using Eq (2), it may be represented as $$G(V_{max}) = \sum\nolimits_{i \ne w} \frac{z_i(k_i - 1)}{k_i} + z_w \ge 0.$$

This can be reduced to $$G(V_{max}) = \sum\nolimits_{i \ne w} \frac{z_i}{k_i} \le 1$$

when an oleic phase does not exist. So, in absence of a water phase, an oleic phase exists when $$\sum\nolimits_{i \ne w} \frac{z_i}{k_i} > 1 \qquad \text{Eq. (10)}$$

The following table summarizes the phase stability check for a multi-component mixture.

TABLE 2

| Stability check for a multi-component mixture | | |
|---|---|---|
| Check W > 0 | $\dfrac{z_w}{k_w} > 1$ or $G\!\left(\dfrac{z_w}{k_w}\right) < 0$ | |
| | W > 0 | W = 0 |
| Check V > 0 | $\displaystyle\sum_{i \neq w} z_i k_i > pq$ | $\displaystyle\sum_{i \neq w} z_i k_i > 1$ |
| Check L > 0 | $\displaystyle\sum_{i \neq w} \dfrac{z_i}{k_i} > \dfrac{p}{q}$ | $\displaystyle\sum_{i \neq w} \dfrac{z_i}{k_i} > 1$ |

In some embodiments, the mass balance function G(V) described herein may be a Rachford-Rice function.

Applications

Use and Implementation in a Reservoir Simulator

Figure 3:
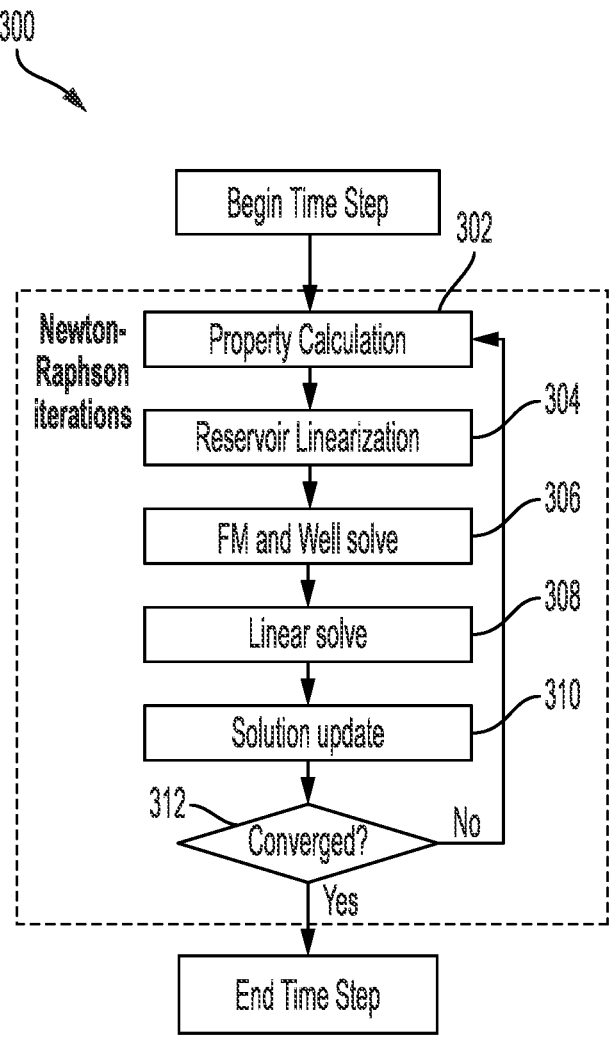
FIG. 3 illustrates a static workflow of a nonlinear cycle for solving a system of nonlinear mass and energy conservation equations using a Newton-Raphson method, in accordance with some embodiments.

In some embodiments, the approaches described herein can be used and implemented in a reservoir simulator, such as INTERSECT (IX). FIG. 3 illustrates a static workflow 300 of a nonlinear cycle for solving a system of nonlinear mass and energy conservation equations using a Newton-Raphson method, in accordance with some embodiments. In that regard, the simulator may solve a system of nonlinear mass and energy conservation equations using a Newton-Raphson method. Predictions are made in time where a sequence of time-step sizes is chosen such that the simulator may converge the equations over a single step, as shown in blocks 302-308 and 312. These equations are calculated using independent variables where derivatives with respect to these variables together with equation residuals form a linear system. After solution of the system, the independent variables are updated and the nonlinear cycle repeats until the residuals are forced to be approximately zero, as shown in block 310.

During this cycle, oil/water/gas phases appear and disappear. Phase appearance is determined by performing a stability check on an existing phase. These results are used as an initial guess for the next iteration of the cycle.

Figure 4A:
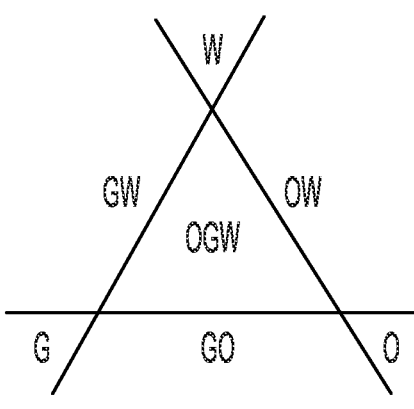
FIG. 4A illustrates a schematic diagram of seven general states of a fluid, in accordance with some embodiments.
Figure 4B:
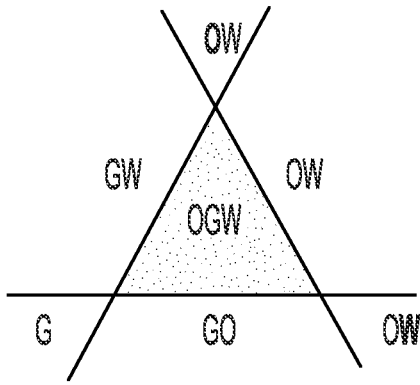
FIG. 4B illustrates a schematic diagram of five general states of a fluid system recognized by simulators, in accordance with some embodiments.

FIG. 4A depicts that, in general, there are seven phase states (oleic (O), gas (G), aqueous (W), oleic-aqueous (OW), gas-oleic (GO), gas-aqueous (GW), oleic-gas-aqueous (OGW)) of a fluid system. However, FIG. 4B depicts some simulators only recognizing five of these phase states (gas (G), oleic-aqueous (OW), gas-oleic (GO), gas-aqueous (GW), oleic-gas-aqueous (OGW)). Note the pure oleic phase state (O) and pure aqueous phase state (W) may not be recognized by simulators.

In general, some reservoir simulators may use natural variables as a primary variable and try to find a solution for these variables at every simulation time-step. The natural variables may be pressure, phase saturations, and component mole fractions in each phase. In thermal simulations, temperature may also be a primary variable. To conform to the simulator architecture, the following table explains how the stability test is used for phase appearance which is leading to another phase state. The proposed stability check can be used in two different ways in reservoir simulators to provide phase appearance information and a proper initial guess for the next simulation cycle.

TABLE 3

| | | Phase transition determination with stability check. | |
|---|---|---|---|
| Transition | Existing Phases | Flash Stability Test | IX Stability Test |
| OW → OWG | W > 0 & L > 0 | $\displaystyle\sum_{i \neq w} z_i k_i > pq$ | $\displaystyle\sum_{i \neq w} x_i k_i + k_w > 1$ |
| GW → OWG | W > 0 & V > 0 | $\displaystyle\sum_{i \neq w} \dfrac{z_i}{k_i} > \dfrac{p}{q}$ | $\displaystyle\sum_{i \neq w} \dfrac{y_i}{k_i} > 1$ |
| GO → OWG | L > 0 & V > 0 | $\dfrac{z_w}{k_w} > 1$ | $\dfrac{y_w}{k_w} > 1$ |
| G → OWG | V > 0 | $\dfrac{z_w}{k_w} > 1$ & $\displaystyle\sum_{i \neq w} \dfrac{z_i}{k_i} > 1$ | $\dfrac{y_w}{k_w} > 1$ & $\displaystyle\sum_{i \neq w} \dfrac{y_i}{k_i} > 1$ |
| G → GO | V > 0 | $\displaystyle\sum_{i \neq w} \dfrac{z_i}{k_i} > 1$ | $\displaystyle\sum_{i \neq w} \dfrac{y_i}{k_i} > 1$ |
| G → GW | V > 0 | $\dfrac{z_w}{k_w} > 1$ | $\dfrac{y_w}{k_w} > 1$ |
| W → GW | W > 0 | $k_w > 1$ | $k_w > 1$ |
| O → GO | L > 0 | $\displaystyle\sum_{i \neq w} z_i k_i > 1$ | $\displaystyle\sum_{i \neq w} x_i k_i > 1$ |

In a first approach, a global mole fraction of components, i.e.; $z_i$, may be computed from the primary variables, i.e.; $P, T, S_w, S_g, x_i, y_i$, and then a stability check similar to the third column of Table 3 is performed. The performed stability check may determine the number of phases and then an iso-thermal flash is performed to calculate a component mole fraction in each phase. The results of the new flash calculation may be used as an initial guess for the next simulation cycle.

The first approach may require an iso-thermal multi-phase flash calculation which leads to problems when the fluid phase envelope is very narrow or pressure and temperature are not linearly independent. In thermal operations such as Steam-Assisted Gravity Drainage (SAGD) or Steam Flooding (SF), it is common to have regions around injectors with pure steam and water and only trace amounts of hydrocarbon. These regions have very narrow phase envelopes and iso-thermal flash calculations fail in these regions. Flash calculation are computationally expensive when applied to millions of grid blocks in thousands of simulation cycles. Another problem with this approach is that the primary variables of the simulator, i.e.; $x_i, y_i$ are over-written by flash calculation results for the component mole fraction and this could cause convergence problems for a non-linear solver.

In some embodiments, the results of the stability check may be used to construct the initial guess for the next simulation cycle based on the results of the performed stability check. In this approach, a stability check may be performed on the primary variables of a simulation, which are provided in the fourth column of Table 3. This approach may not require any flash calculation and is therefore robust, computationally inexpensive and may not over-write the results of the simulator's primary variables by flash calculation results. The component mole fraction of phase as calculated is constructed from the results of the stability check and the computation of global mole fraction is not required.

Performing the stability check on the simulator's primary variables may be equivalent to performing the stability check on global mole fractions (fourth column of Table 3 is equivalent to the third column of Table 4, shown below). When one considers the transition from OW→OWG case, one should test the gas phase appearance from the OW phase state using the following equation: $\Sigma_{i\neq w}x_ik_i+k_w>1$ check. Note, $k_w$ and $k_i$ are only functions of temperature and pressure and $x_i$ may be the simulator's primary variables. At bubble point, $L=1-W=1-z_w$ and $x_i$ can be written as $$x_i = \frac{z_i}{1-z_w}$$

and by plugging it into Eq. (10), we have the following equation:

$$\sum_{i\neq w}\frac{z_ik_i}{1-z_w}+k_w>1 \qquad \text{Eq. (11)}$$

By a simple algebraic manipulation, one can re-write Eq (11) to a different form, $\Sigma_{i\neq w}z_ik_i>pq$, which is identical to the stability check for gas phase appearance in presence of water and oil phases. The results of the stability check could also be used to calculate the component mole fractions for the new phase. In the next cycle one may set $y_i^*=k_ix_i$ an $y_w^*=k_w$, so that the component mole fraction of the phase which appears may be normalized to satisfy the $\Sigma_iy_i=1$ condition. Table 4 summarizes possible phase transitions in INTERSECT (IX), the proper stability check, and construction of component mole fraction of phase which appears for the next simulation cycle.

TABLE 4

Reservoir Simulator stability check and component mole fraction construction for appeared phase

| Transition | IX Stability Test | Component Mole Fraction of Appeared Phase |
|---|---|---|
| OW → OWG | $\sum_{i\neq w}x_ik_i+k_w>1$ | $y_i=x_ik_i$ & $y_w=k_w$ |
| GW → OWG | $\sum_{i\neq w}\frac{y_i}{k_i}>1$ | $x_i=\frac{y_i}{k_i}$ |
| GO → OWG | $\frac{y_w}{k_w}>1$ | $y_w=k_w$ |
| G → OWG | $\frac{y_w}{k_w}>1$ & $\sum_{i\neq w}\frac{y_i}{k_i}>1$ | $x_i=\frac{y_i}{k_i}$ & $y_w=k_w$ |
| G → GO | $\sum_{i\neq w}\frac{y_i}{k_i}>1$ | $x_i=\frac{y_i}{k_i}$ |
| G → GW | $\frac{y_w}{k_w}>1$ | $y_w=k_w$ |
| W → GW | $k_w>1$ | $y_w=k_w$ |
| O → GO | $\sum_{i\neq w}x_ik_i>1$ | $y_i=x_ik_i$ |

FIG. 5 is a workflow 500 illustrating a method for determining a phase state of a thermal compositional fluid sample, in accordance with some embodiments. In block 502, the method includes providing, using one or more computing device processors, a first set of parameters from an oilfield operation (e.g., data collected in accordance with FIGS. 1-2) for a thermal compositional fluid sample. At block 504, the method includes constructing, using the one or more computing device processors, a mass balance function for testing whether a phase of the thermal compositional fluid sample exists based on the first of parameters. At block 506, the method includes inputting, using the one or more computing device processors, a sequence of time-steps to a numerical iterations technique based on the mass balance function. At block 508, the method includes solving, using the one or more computing device processors, a system of nonlinear mass and energy conservation equations associated with the thermal compositional fluid sample using the numerical iterations technique.

At block 510, the method includes determining, using the one or more computing device processors, whether the system of nonlinear mass and energy conservation equations converges over a single step to provide a first solution to the system of nonlinear mass and energy conservation equations. In response to the system of nonlinear mass and energy conservation equations converging, the method includes determining, using the one or more computing device processors, an existing phase state of the thermal compositional fluid sample as indicated by the first solution, as shown at block 512. In response to determining the existing phase state, the method includes performing, using the one or more computing device processors, a stability test on the existing phase of the thermal compositional fluid sample based on the first solution, as shown at block 514. At block 516, the method includes determining, using the one or more computing device processors, whether the thermal compositional fluid sample includes an appearance of a new phase state based on results from the stability test.

At block 518, the method includes updating, using the one or more computing device processors, the first set parameters based on the results from the stability test to be applied to a next iteration of the numerical iterations technique.

FIG. 6 is a workflow 600 illustrating another method for determining a phase state of a thermal compositional fluid sample, in accordance with some embodiments. In block 602, the method includes providing, using one or more computing device processors, a first set of parameters from an oilfield operation (e.g., data collected in accordance with FIGS. 1-2) for a thermal compositional fluid sample. At block 604, the method includes constructing, using the one or more computing device processors, a mass balance function for testing whether a phase of the thermal compositional fluid sample exists based on the first of parameters. At block 606, the method includes providing, using the one or more computing device processors, a first set of equilibrium k-values for one or more hydrocarbon components of the thermal compositional fluid sample between an oleic phase and a gaseous phase based on the mass balance function. At block 608, the method includes providing, using the one or more computing device processors, a second equilibrium k-value for a water component of the thermal compositional fluid sample between an aqueous phase and the gaseous phase.

At block 610, the method includes determining, using the one or more computing device processors, a current phase state of the thermal compositional fluid sample based on the first set of equilibrium k-values and the second equilibrium k-value. In response to determining the current phase state of the thermal compositional fluid sample, the method includes determining, using the one or more computing device processors, whether the thermal compositional fluid sample includes an appearance of a new phase state based on the current phase state of the thermal compositional fluid sample, as shown at block 612.

Figure 7:
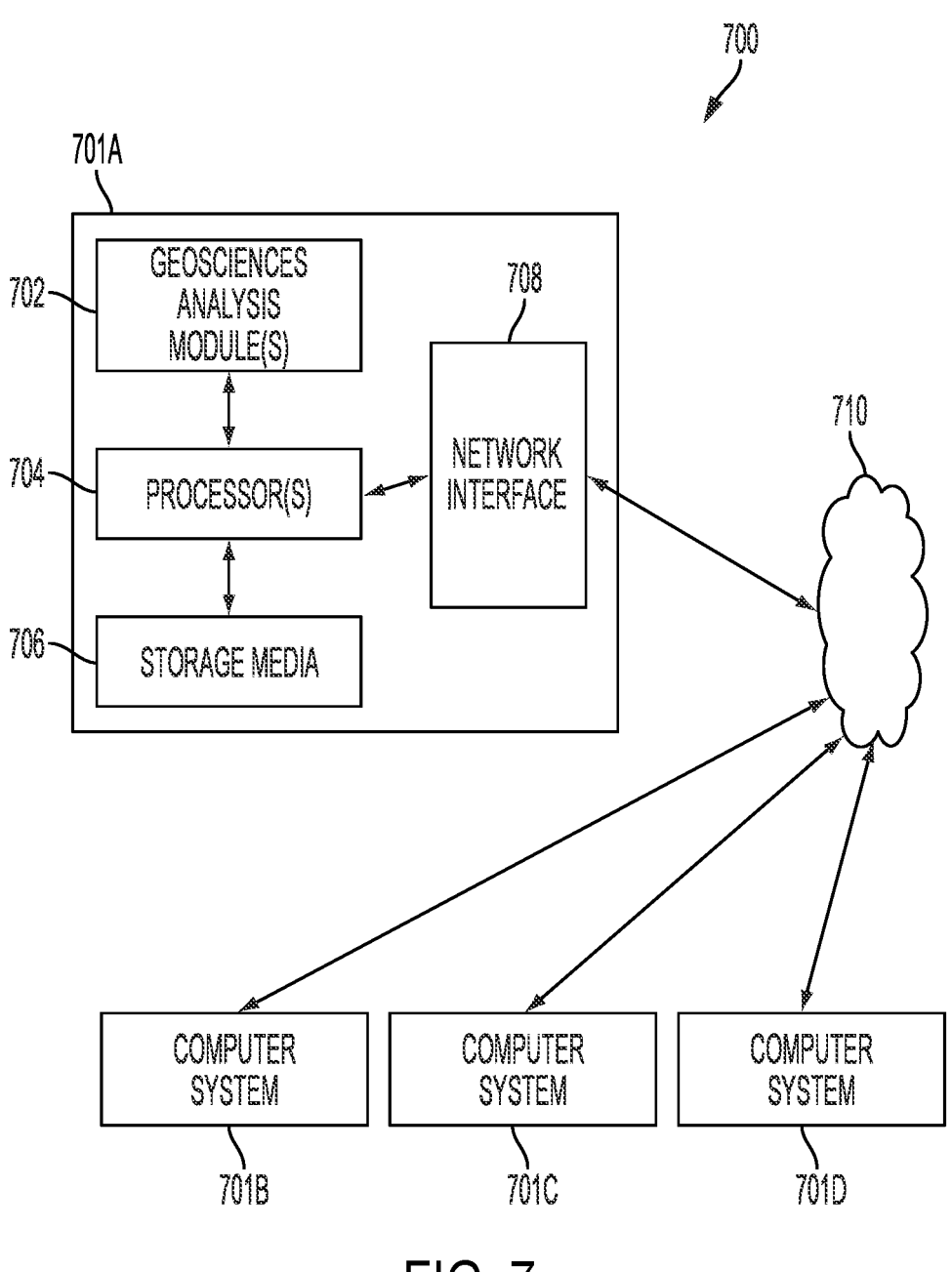
FIG. 7 illustrates an example of a computing system for carrying out some of the methods of the present disclosure, in accordance with some embodiments.

FIG. 7 depicts an example computing system 700 in accordance with carrying out some of the methods of the present disclosure, in accordance with some embodiments. For example, the computing system 700 may perform the workflows 500 and 600 described herein.

The computing system 700 can be an individual computer system 701A or an arrangement of distributed computer systems. The computer system 701A includes one or more geosciences analysis modules 702 that are configured to perform various tasks according to some embodiments, such as one or more methods disclosed herein. To perform these various tasks, geosciences analysis module 702 executes independently, or in coordination with, one or more processors 704, which is (or are) connected to one or more storage media 706. The processor(s) 704 is (or are) also connected to a network interface 708 to allow the computer system 701A to communicate over a data network 710 with one or more additional computer systems and/or computing systems, such as 701B, 701C, and/or 701D (note that computer systems 701B, 701C and/or 701D may or may not share the same architecture as computer system 701A, and may be located in different physical locations, e.g., computer systems 701A and 701B may be on a ship underway on the ocean, while in communication with one or more computer systems such as 701C and/or 701D that are located in one or more data centers on shore, other ships, and/or located in varying countries on different continents). Note that data network 710 may be a private network, it may use portions of public networks, it may include remote storage and/or applications processing capabilities (e.g., cloud computing).

A processor can include a microprocessor, microcontroller, processor module or subsystem, programmable integrated circuit, programmable gate array, or another control or computing device.

The storage media 706 can be implemented as one or more computer-readable or machine-readable storage media. Note that while in the example embodiment of FIG. 7 storage media 706 is depicted as within computer system 701A, in some embodiments, storage media 706 may be distributed within and/or across multiple internal and/or external enclosures of computing system 701A and/or additional computing systems. Storage media 706 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs), BluRays or any other type of optical media; or other types of storage devices. "Non-transitory" computer readable medium refers to the medium itself (i.e., tangible, not a signal) and not data storage persistency (e.g., RAM vs. ROM).

Note that the instructions or methods discussed above can be provided on one computer-readable or machine-readable storage medium, or alternatively, can be provided on multiple computer-readable or machine-readable storage media distributed in a large system having possibly plural nodes and/or non-transitory storage means. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions or located at a remote site from which machine-readable instructions can be downloaded over a network for execution.

It should be appreciated that computer system 701A is one example of a computing system, and that computer system 701A may have more or fewer components than shown, may combine additional components not depicted in the example embodiment of FIG. 7, and/or computer system 701A may have a different configuration or arrangement of the components depicted in FIG. 7. The various components shown in FIG. 7 may be implemented in hardware, software, or a combination of both, hardware and software, including one or more signal processing and/or application specific integrated circuits.

It should also be appreciated that while no user input/output peripherals are illustrated with respect to computer systems 701A, 701B, 701C, and 701D, many embodiments of computing system 700 include computing systems with keyboards, touch screens, displays, etc. Some computing systems in use in computing system 700 may be desktop workstations, laptops, tablet computers, smartphones, server computers, etc.

Further, the steps in the processing methods described herein may be implemented by running one or more functional modules in an information processing apparatus such as general-purpose processors or application specific chips, such as ASICs, FPGAs, PLDs, or other appropriate devices. These modules, combinations of these modules, and/or their combination with general hardware are included within the scope of protection of the disclosure.

In some embodiments, a computing system is provided that comprises at least one processor, at least one memory, and one or more programs stored in the at least one memory, wherein the programs comprise instructions, which when executed by the at least one processor, are configured to perform any method disclosed herein.

In some embodiments, a computer readable storage medium is provided, which has stored therein one or more programs, the one or more programs comprising instructions, which when executed by a processor, cause the processor to perform any method disclosed herein.

In some embodiments, a computing system is provided that comprises at least one processor, at least one memory, and one or more programs stored in the at least one memory; and means for performing any method disclosed herein.

In some embodiments, an information processing apparatus for use in a computing system is provided, and that includes means for performing any method disclosed herein.

In some embodiments, a graphics processing unit is provided, and that includes means for performing any method disclosed herein.

Simulators as discussed herein may be used to run field development planning cases in the oil and gas industry. These involve running of thousands of such cases with slight variations in the model setup. Embodiments described herein can be applied readily to such applications and the resulting gains are significant.

The embodiments described herein can be used for standalone simulations or closed loop optimization routines and can be implemented as an on-premise standalone solution as well as a cloud solution.

While various embodiments in accordance with the disclosed principles have been described above, it should be understood that they have been presented by way of example only and are not limiting.

Furthermore, the above advantages and features are provided in described embodiments, but shall not limit the application of such issued claims to processes and structures accomplishing any or all of the above advantages.

The invention claimed is:

1. A method for determining a phase state of a thermal compositional fluid sample comprising:

providing, using one or more computing device processors, a first set of parameters from an oilfield operation for a thermal compositional fluid sample;

constructing, using the one or more computing device processors, a monotonic mass balance function for testing whether a phase of the thermal compositional fluid sample exists based on the first set of parameters;

inputting, using the one or more computing device processors, a sequence of time-iterations to a numerical iterations technique based on the monotonic mass balance function;

solving, using the one or more computing device processors, a system of nonlinear mass and energy conservation equations associated with the thermal compositional fluid sample using the numerical iterations technique;

determining, using the one or more computing device processors, whether the system of nonlinear mass and energy conservation equations converges over a single numerical iteration to provide a first solution to the system of nonlinear mass and energy conservation equations;

in response to the system of nonlinear mass and energy conservation equations converging, determining, using the one or more computing device processors, an existing phase state of the thermal compositional fluid sample as indicated by the first solution;

in response to determining the existing phase state, performing, using the one or more computing device processors, a stability test on the existing phase state of the thermal compositional fluid sample based on the first solution;

determining, using the one or more computing device processors, whether the thermal compositional fluid sample includes an appearance of a new phase state based on results from the stability test;

updating, using the one or more computing device processors, the first set of parameters based on the results from the stability test; and controlling, based on the existing phase state, an actuation of a drilling tool performing the oilfield operation.

2. The method of claim 1, wherein providing the first set of parameters comprises providing pressure, temperature, or molar rate of the thermal compositional fluid sample.

3. The method of claim 1, wherein constructing the monotonic mass balance function comprises constructing the monotonic mass balance function in a gas phase split.

4. The method of claim 1, wherein inputting the sequence of time-iterations to the numerical iterations technique comprises providing an initial time-iteration to form the sequence of time-iterations.

5. The method of claim 1, wherein inputting the sequence of time-iterations to the numerical iterations technique comprises utilizing a Newton-Raphson numerical technique.

6. The method of claim 1, wherein solving the system of nonlinear mass and energy conservation equations comprises utilizing the system of nonlinear mass and energy conservation equations to test for existence of oleic, gaseous and aqueous phases in the thermal compositional fluid sample.

7. The method of claim 1, wherein performing the stability test comprises confirming a simulator architecture associated with performing the stability test.

8. The method of claim 1, wherein performing the stability test comprises performing the stability test on a set of primary variables used by a simulator.

9. The method of claim 7, wherein performing the stability test comprises computing a component mole fraction for the new phase state and the existing phase state based on the stability test.

10. A system for determining a phase state of a thermal compositional fluid sample, the system comprising:

one or more computing device processors; and one or more computing device memories, coupled to the one or more computing device processors, the one or more computing device memories storing instructions executed by the one or more computing device processors, wherein the instructions are configured to:

provide a first set of parameters from an oilfield operation for a thermal compositional fluid sample;

construct a monotonic mass balance function for testing whether a phase of the thermal compositional fluid sample exists based on the first set of parameters;

input a sequence of time-iterations to a numerical iterations technique based on the monotonic mass balance function;

solve a system of nonlinear mass and energy conservation equations associated with the thermal compositional fluid sample using the numerical iterations technique;

determine whether the system of nonlinear mass and energy conservation equations converges over a single numerical iteration to provide a first solution to the system of nonlinear mass and energy conservation equations;

in response to the system of nonlinear mass and energy conservation equations converging, determine an existing phase state of the thermal compositional fluid sample as indicated by the first solution;

in response to determining the existing phase state, perform a stability test on the existing phase state of the thermal compositional fluid sample based on the first solution;

determine whether the thermal compositional fluid sample includes an appearance of a new phase state based on results from the stability test;

update the first set of parameters based on the results from the stability test; and control, based on the existing phase state, actuation of a drilling tool performing the oilfield operation.

11. The system of claim 10, wherein the first set of parameters comprises pressure, temperature, or molar rate of the thermal compositional fluid sample.

12. The system of claim 10, wherein the monotonic mass balance function is in a gas phase split.

13. The system of claim 10, wherein the sequence of time-iterations comprises an initial time-iteration to form the sequence of time-iterations.

14. The system of claim 10, wherein the numerical iterations technique is a Newton-Raphson numerical technique.

15. The system of claim 10, wherein the system of nonlinear mass and energy conservation equations are used to test for existence of oleic, gaseous and aqueous phases in the thermal compositional fluid sample.

16. The system of claim 10, wherein the stability test is used to compute a mole fraction for the new phase state and the existing phase state.

17. The system of claim 10, wherein the stability test requires identifying a simulator architecture used for performing the stability test.

18. The system of claim 10, wherein the stability test is performed on a set of primary variables used by a simulator.

* * * * *